(12) United States Patent
Weis

(10) Patent No.: US 11,612,917 B2
(45) Date of Patent: Mar. 28, 2023

(54) METHOD FOR OPERATING A RECONDITIONING APPARATUS AND A MEDICAL SYSTEM

(71) Applicant: OLYMPUS WINTER & IBE GMBH, Hamburg (DE)

(72) Inventor: Antonia Weis, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 109 days.

(21) Appl. No.: 17/217,597

(22) Filed: Mar. 30, 2021

(65) Prior Publication Data

US 2021/0213492 A1    Jul. 15, 2021

Related U.S. Application Data

(60) Division of application No. 16/434,776, filed on Jun. 7, 2019, now Pat. No. 10,994,314, which is a continuation of application No. PCT/EP2017/082959, filed on Dec. 15, 2017.

(30) Foreign Application Priority Data

Dec. 21, 2016  (DE) .................... 10 2016 225 884.2

(51) Int. Cl.
| | |
|---|---|
| *B08B 9/032* | (2006.01) |
| *A61B 90/70* | (2016.01) |
| *A61B 90/90* | (2016.01) |
| *A61B 90/96* | (2016.01) |
| *A61B 90/98* | (2016.01) |
| *A61B 1/12* | (2006.01) |

(52) U.S. Cl.
CPC ............ *B08B 9/0328* (2013.01); *A61B 90/70* (2016.02); *A61B 90/90* (2016.02); *B08B 9/0325* (2013.01); *A61B 1/125* (2013.01); *A61B 90/96* (2016.02); *A61B 90/98* (2016.02); *A61B 2090/701* (2016.02); *B08B 2209/032* (2013.01)

(58) Field of Classification Search
None
See application file for complete search history.

(56) References Cited

FOREIGN PATENT DOCUMENTS

EP          2740401 A1 * 6/2014   ......... A61B 1/00006

* cited by examiner

*Primary Examiner* — Eric W Golightly
(74) *Attorney, Agent, or Firm* — Scully, Scott, Murphy & Presser, P.C.

(57) ABSTRACT

A method for operating a reconditioning apparatus for cleaning and disinfecting a medical instrument(s), the medical instrument having an internal channel(s). The method including: receiving the medical instrument(s) in a reconditioning chamber; connecting the internal channel(s) to a fluid connection of fluid connections in the reconditioning chamber; flushing the internal channel(s) with a reconditioning fluid; detecting an identifying feature of medical instrument(s) indicating a type of the medical instrument(s); comparing the detected type with data sets stored in a database and, of the fluid connections, provide an allocation of a fluid connection connected to the internal channel(s) on a basis of the identified type; and subsequent to the flushing, actuating a compressed air source to apply compressed air to the allocated fluid connection such that reconditioning fluid present in the at least one internal channel is blown out of the channel.

6 Claims, 2 Drawing Sheets

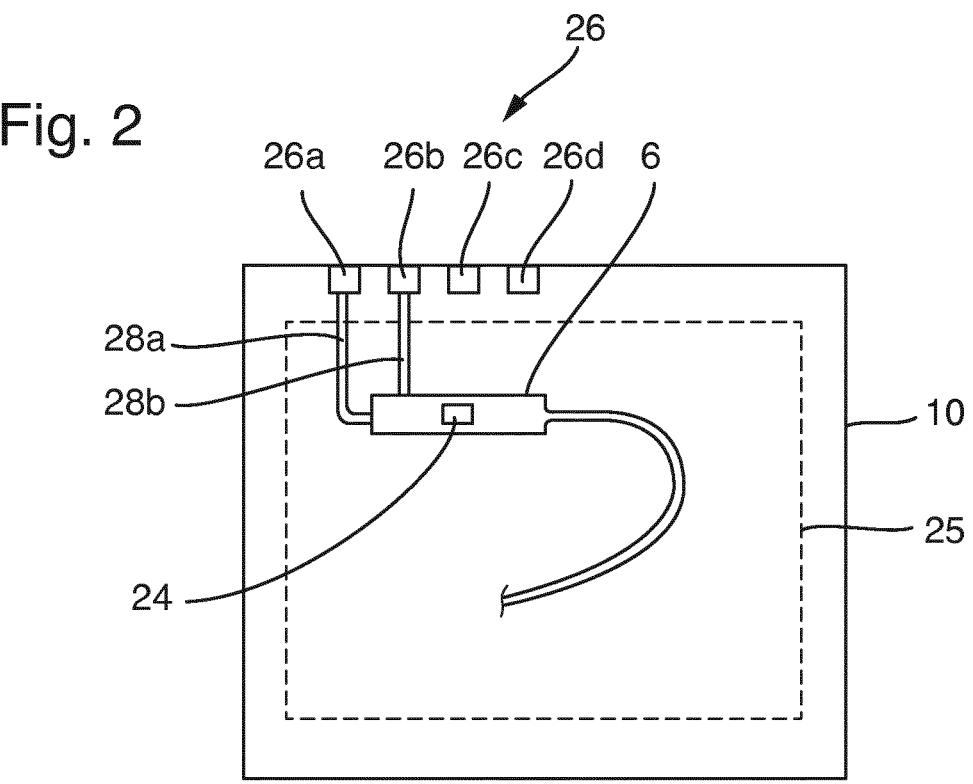

METHOD FOR OPERATING A RECONDITIONING APPARATUS AND A MEDICAL SYSTEM

CROSS-REFERENCE TO RELATED APPLICATION

The present application is a divisional application of U.S. application Ser. No. 16/434,776 filed on Jun. 7, 2019, and issued as U.S. Pat. No. 10,994,314 on May 4, 2021, which is a continuation of PCT/EP2017/082959 filed on Dec. 15, 2017, which is based upon and claims the benefit to DE 10 2016 225 884.2 filed on Dec. 21, 2016, the entire contents of each of which are incorporated herein by reference.

BACKGROUND

Field

The present disclosure relates to a method for operating a reconditioning apparatus for cleaning and disinfecting at least one medical instrument which has at least one internal channel, wherein the medical instrument is received in a reconditioning chamber of the reconditioning apparatus during the reconditioning and the at least one internal channel is connected to a fluid connection of a plurality of fluid connections being present in the reconditioning chamber, wherein the channel is flushed during the reconditioning with a reconditioning fluid. The present disclosure also relates to a method for operating a medical system, comprising a reconditioning apparatus for reconditioning at least one medical instrument, and to a medical instrument having at least one internal channel. In addition to this, the present disclosure relates to a reconditioning apparatus for cleaning and disinfecting at least one medical instrument having at least one internal channel, wherein the reconditioning apparatus comprises a reconditioning chamber which is configured to receive the medical instrument during the reconditioning, and wherein the at least one internal channel is connected to one fluid connection of a plurality of fluid connections present in the reconditioning chamber in order to flush the channel with a reconditioning fluid. Likewise, the present disclosure relates to a medical system comprising a reconditioning apparatus.

Prior Art

High demands are made on the reconditioning of medical devices and instruments, for example on medical instruments such as endoscopes. Following the use of the medical instruments, these are disinfected and/or cleaned in a cleaning and/or disinfection device which is in general referred to as a reconditioning apparatus. During the reconditioning, the medical instrument is located in a reconditioning chamber of the reconditioning apparatus. Such a reconditioning apparatus for endoscopes is known, for example, by the name ETD (Endo Thermo Disinfector) and is manufactured by OLYMPUS Winter & Ibe GmbH, Hamburg.

Internal channels of medical instruments, for example internal working channels of endoscopes, are frequently cleaned during the reconditioning by means of flushing with a cleaning and/or disinfecting solution. A cleaning and/or disinfecting solution is in general referred to as a reconditioning fluid. In order to conduct the reconditioning fluid through the internal channels of the medical instrument, the latter is connected to one or more fluid connections which are present in the reconditioning chamber.

The reconditioning of the medical instruments frequently takes place in multiple consecutive flushing steps, in which the internal channels are flushed with various reconditioning fluids. There are various possible ways to minimize the transfer of the alkaline solution, that is to say the transfer of the residual amount of reconditioning fluid of a first flushing step, which remains in the channels following pumping out, to a following, second flushing step. In addition to using cascading piping it is, for example, possible to deploy compressed air in order to eliminate residual amounts of reconditioning fluid.

An apparatus for cleaning medical products, in which compressed air is deployed, is known from DE 10 2014 102 064 A1. This comprises a chamber for receiving the objects to be cleaned and at least one supply line for supplying a cleaning fluid. An appropriate apparatus is provided in order to distribute the cleaning fluid onto or into the objects to be cleaned. Compressed air can be fed into the supply line for the cleaning fluid by means of a valve. A mixture of an aqueous cleaning liquid and compressed air is provided as the cleaning fluid.

Compressed air is a valuable and expensive working fluid, the manufacturing and provision costs of which are underestimated in many cases. It is therefore always worth striving for a way to handle this resource economically.

SUMMARY

It is an object to provide a method for operating a reconditioning apparatus, a method for operating a medical system, a reconditioning apparatus for cleaning and disinfecting at least one medical instrument as well as a medical system, wherein an economical way of handling compressed air as the process fluid is striven for. In connection with this, the structural limits of the resource compressed air, for example with respect to the available volume flow of the compressed air, are further to be observed.

Such object can be achieved by a method for operating a reconditioning apparatus for cleaning and disinfecting at least one medical instrument which has at least one internal channel, wherein the medical instrument is received in a reconditioning chamber of the reconditioning apparatus during the reconditioning and the at least one internal channel is connected to a fluid connection of a plurality of fluid connections being present in the reconditioning chamber, wherein the channel is flushed during the reconditioning with a reconditioning fluid, wherein the reconditioning apparatus comprises a control unit, a compressed air unit, a database and an input unit for detecting an identifying feature, wherein a plurality of data sets are stored in the database, which each comprise information relating to an allocation of the fluid connections present in the reconditioning chamber to a specific type of a medical instrument, wherein the identifying feature of the medical instrument is detected with the input unit, on which information relating to its type is stored, the control unit compares the type of the medical instrument identified on the basis of the detected information with data sets present in the database and thus establishes an allocation of the fluid connection connected to the internal channel on the basis of the identified type and actuates the compressed air unit in that the latter applies a shot of compressed air to the allocated fluid connection, such that reconditioning fluid present in the flushed internal channel of the medical instrument is blown out of the channel.

The method for operating the reconditioning apparatus can use only as much compressed air as is actually necessary to achieve the desired technical effect. Therefore, in other words, compressed air is not wasted. Likewise, the requirements can reduce with respect to the volume flow of the compressed air to be provided by the infrastructure. For example, the compressed air system no longer has to be designed for peak airflows which rarely occur, since these no longer occur or only do so to a reduced extent. A high consumption of compressed air results in high operating costs. These costs can be lowered with the method for operating the reconditioning apparatus. The compressed air is applied to the fluid connections, knowing the allocation of these connections to the connected flushing product, such as, the medical instrument. The compressed air can be applied only to those connections which are actually flushed during the reconditioning with reconditioning fluid and are therefore blown out in order to reduce the transfer of the alkaline solution.

A number of fluid connections can be present in the reconditioning chamber. Since the type of the reconditioned medical instrument is detected individually, the shot of compressed air can only be applied to those fluid connections, that is to say that partial quantity of the fluid connections present, which are also allocated to the appropriate type of medical instrument. Thus, the shot of compressed air does not have to be applied to all of the fluid connections. With this process, a part of the deployed compressed air can escape via the unallocated fluid connections, unused, into the reconditioning chamber. This would be a waste of compressed air, which would increase the operating costs of the reconditioning apparatus needlessly and to no avail.

The identifying feature can be detected by a manual input. In such a case, the input unit can be a keyboard, a number pad or the like.

According to an embodiment, the reconditioning of the medical instrument can comprise multiple flushing steps, wherein the shot of compressed air is applied to the at least one allocated fluid connection between two consecutive flushing steps. The blending of the reconditioning fluids, as they are deployed during the consecutive flushing steps, can be considerably reduced.

In addition, fluid connections which are not allocated to the identified type of medical instrument can be shut off at least for the duration of the shot of compressed air, such that no compressed air escapes from the unallocated fluid connections. Thus, compressed air can only be applied to those fluid connections which are connected fluidically to an internal channel of the medical instrument during the shot of compressed air.

In addition, following the termination of the cleaning and disinfecting process, that is to say following the termination of the reconditioning process, the shot of compressed air can be applied to the connected fluid connections. Such a measure can be provided, in order to dry the internal channels.

According to another embodiment, a further shot of compressed air can be applied to fluid connections which are not allocated to the identified type of medical instrument, wherein this further shot of compressed air can last a shorter time than the shot of compressed air, with which the at least one flushed internal channel of the medical instrument is blown out. The comparison between the shot of compressed air and the further shot of compressed air can be effected with respect to the temporal duration of the two shots of compressed air and, can be at the same pressure. In other words, the further shot of compressed air can have a smaller mass than the shot of compressed air. The further shot of compressed air serves to blow out cleaning fluid which collects in the unallocated fluid connections during the reconditioning process, so that the system is as clean as possible at the end of the reconditioning process. A shorter temporal duration can be used for the further shot of compressed air, since potentially less fluid is present in the unallocated fluid connections than in the allocated connections.

The identifying feature of the medical instrument can be a machine-readable identifying feature and the input unit can be a reading device for detecting the machine-readable identifying feature, wherein the identifying feature can be detected by being read out by the reading device. The machine-readable identifying feature can be a RFID tag, a barcode or a QR code.

In the context of the present description, a "fluid connection" is a connection for, for example, a coupling connected to a hose, at which a fluid, that is to say a liquid, a gas or a liquid-gas-mixture, is provided. A fluid connection is, for example, a connection to which a quick coupling of a hose can be coupled, through which a reconditioning fluid is conducted, and which can be coupled with its opposite end to an endoscope. The term "coupled fluidically" denotes an indirect or direct connection for a fluid, for example a pipe or a hose for the working fluid.

Such object can be further achieved by a method for operating a medical system, comprising a reconditioning apparatus for reconditioning at least one medical instrument, and a medical instrument having at least one internal channel, wherein the medical system is operated in accordance to a method according to one or more of the previously indicated aspects.

The same or similar advantages apply to the method for operating the medical system as have already been mentioned with respect to the method for operating the reconditioning apparatus.

In addition, such object can be achieved by a reconditioning apparatus for cleaning and disinfecting at least one medical instrument having at least one internal channel, wherein the reconditioning apparatus comprises a reconditioning chamber which is configured to receive the medical instrument during the reconditioning, and wherein the at least one internal channel is connected to one fluid connection of a plurality of fluid connections present in the reconditioning chamber in order to flush the channel with a reconditioning fluid, wherein the reconditioning apparatus comprises a control unit, a compressed air unit, a database and an input unit for detecting an identifying feature, wherein a plurality of data sets are stored in the database, which each comprise information relating to an allocation of the fluid connections present in the reconditioning chamber to a specific type of a medical instrument, and wherein the input unit is configured to detect the identifying feature of the medical instrument, in which information relating to the type of the medical instrument is stored, wherein the control unit is further configured to compare the type of the medical instrument identified on the basis of the read-out information with data sets present in the database and thus establish an allocation of the fluid connection connected to the internal channel on the basis of the identified type and, in addition, to actuate the compressed air unit such that the latter applies a shot of compressed air to the allocated fluid connection, such that reconditioning fluid present in the flushed internal channel of the medical instrument can be blown out from the channel.

The same or similar advantages also apply to the reconditioning apparatus, as have already been indicated with respect to the method for operating the reconditioning apparatus. The reconditioning apparatus can only require a very small quantity of compressed air as the process fluid. For this reason, the reconditioning apparatus can be very economical with respect to its operating costs.

According to another embodiment, the control unit can be further configured to apply a further shot of compressed air to fluid connections which are not allocated to the identified type of medical instrument, wherein this further shot of compressed air can last a shorter time than the shot of compressed air which is applied to the at least one allocated fluid connection.

The control unit can be configured to identify which fluid connections are allocated to the medical instrument and which are not. The control unit obtains this information from the information stored in the identifying feature.

In another embodiment, the reconditioning apparatus can be configured in such a manner that the identifying feature of the medical instrument can be a machine-readable identifying feature and the input unit can be a reading device for detecting the machine-readable identifying feature, wherein the control unit can be further configured to detect the identifying feature in that it is read out by the reading device. The reading device can comprise a RFID reader, a barcode scanner or the like.

In addition, such object can be achieved by a medical system, comprising a reconditioning apparatus according to one or more of the previously indicated aspects. In addition, the medical system can comprise at least one medical instrument having at least one internal channel, wherein the medical instrument can comprise a machine-readable identifying feature, in which information relating to the type of the medical instrument is stored.

The medical device can be a surgical instrument, such as an endoscope. This relates to all of the embodiments.

Further features will become evident from the description of embodiments, together with the claims and the appended drawings. Embodiments can fulfill individual features or a combination of several features.

BRIEF DESCRIPTION OF THE DRAWINGS

The embodiments will be described below without limiting the general concept of the invention by means of exemplary embodiments with reference to the drawings, wherein reference is expressly made to the drawings regarding all of the details which are not explained in greater detail in the text, wherein:

FIG. 2 illustrates a schematically simplified top view of a reconditioning chamber of a reconditioning apparatus, in which a medical instrument is arranged.

In the drawings, the same or similar elements and/or parts are, in each case, provided with the same reference numerals so that they are not introduced again in each case.

DETAILED DESCRIPTION

Figure 1:
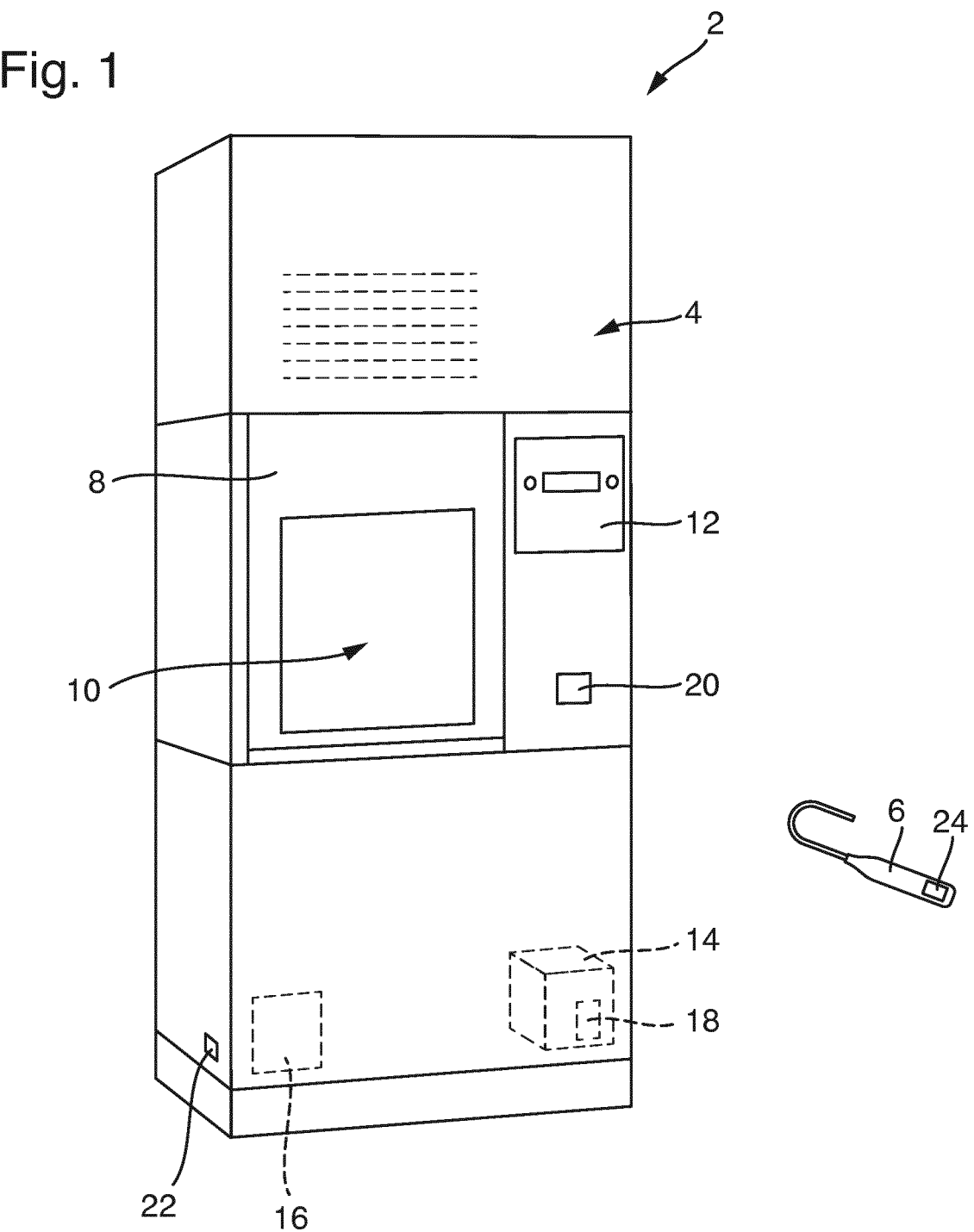
FIG. 1 illustrates a medical system comprising a reconditioning apparatus and a medical instrument in a schematically simplified perspective representation.

FIG. 1 shows, in a simplified, schematic and perspective view, a medical system 2 comprising a reconditioning apparatus 4 and a medical instrument 6. The reconditioning apparatus 4 is configured to clean and/or disinfect at least one medical instrument 6, such as a surgical instrument, for example an endoscope. For this purpose, the reconditioning apparatus 4 comprises a reconditioning chamber 10 behind a door 8. One or more medical instruments 6 are typically arranged in the reconditioning chamber 10 during the reconditioning process. In addition, the reconditioning apparatus 4 comprises an operating unit 12.

In addition, the reconditioning apparatus 4 comprises a control unit 14 (such as a controller including hardware), a compressed air unit 16 (such as a compressed source), a database 18, which can be a part of the control unit 14, as well as an input unit (device) 20 for detecting an identifying feature of the medical instrument 6. The identifying feature is, for example, a serial number or a type number. The identifying feature can be a machine-readable identifying feature. For example, a RFID tag, a barcode and/or a QR code is provided as the machine-readable identifying feature. The identifying feature is input, for example, manually, e.g. via the operating unit 12. If a machine-readable identifying feature is provided, the input unit 20 is, for example, an RFID reader. The compressed air unit 16 of the reconditioning apparatus 4 comprises a compressed air connection 22, via which the reconditioning apparatus 4 is connected to a compressed air supply network. During the reading-out process, the machine-readable identifying feature can be located both inside and outside the reconditioning chamber 10.

The medical instrument 6 which is, for example, an endoscope, has an internal channel, for example a working channel. After the medical instrument 6 has been used, the internal channel must be cleaned or respectively flushed in the channel, which is not represented in the figure, during the reconditioning. The internal channel of the medical instrument 6 is flushed with a reconditioning fluid, for example a cleaning and disinfecting solution or alkaline solution. In addition, the medical instrument 6 comprises an identifying feature 24, such as a machine-readable identifying feature, for example a QR code or a RFID tag.

FIG. 2 shows the reconditioning chamber 10 of the reconditioning apparatus 4 in a schematically simplified top view. The medical instrument 6 is arranged in a schematically represented reconditioning basket 25 which is located inside the reconditioning chamber 10. Multiple fluid connections 26a, 26b, 26c and 26d, which are also to be designated in general with reference numeral 26, are present or respectively arranged in the reconditioning chamber 10. The reconditioning fluid is supplied to the internal channel of the medical instrument 6 via the fluid connections 26. By way of example, the medical instrument 6 represented in FIG. 2 comprises two internal channels (which are not represented). A first internal channel is accordingly coupled fluidically via a first connection hose 28a and the second channel is coupled fluidically via a second connection hose 28b to the first fluid connection 26a or respectively the second fluid connection 26b. The further fluid connections 26c and 26d are not allocated, that is to say they remain free. In the case of the type of the medical instrument 6 represented by way of example, the fluid connections 26a and 26b are considered to be allocated and the fluid connections 26c and 26d are considered to not be allocated. The information about which connections are allocated and which are not is referred to as the allocation of the fluid connections.

In order to recondition the medical instrument 6, the medical instrument 6 is coupled fluidically via the connection hoses 28a, 28b to the fluid connections 26a, 26b. The internal channels of the medical instrument 6 are subsequently flushed with the reconditioning fluid. If the medical instrument 6 which is, for example, already located inside the reconditioning basket 25, is introduced into the reconditioning chamber 10, the input unit 20 of the reconditioning apparatus 4 reads out the machine-readable identifying feature of the medical instrument 6. Alternatively, during loading of the reconditioning apparatus 4, the identifying feature, that is to say for example a serial number or a type number, is manually input via the operating unit 12. A plurality of data sets is stored in the database 18 of the control unit 14, which each comprise information relating to an allocation of the fluid connections 26 present in the reconditioning chamber 10 to the relevant type of a medical instrument 6.

For example, the database 18 therefore comprises a multiplicity of data sets, wherein each individual data set is assigned to a specific type of an endoscope. Information about which of the fluid connections 26 is allocated to the relevant type of the endoscope is stored in this data set. In the represented exemplary embodiment, the associated data set would comprise the information that the endoscope which is represented, by way of example, as the medical instrument 6, is allocated to the first and the second fluid connection 26a, 26b.

This information can be automatically detected if the medical instrument 6 is inserted into the reconditioning chamber 10, in which the machine-readable identifying feature of the medical instrument 6 is specifically read out by the input unit 20. The information relating to the type of the medical instrument 6 placed in the reconditioning chamber 10 is compared by the control unit 14 with the data sets present in the database 18. Thus, an allocation of the fluid connections 26a, 26b connected to the internal channel is then established on the basis of the identified type. The control unit 14 then actuates the compressed air unit 16 in such a manner that a shot of compressed air is applied to the allocated fluid connections 26a, 26b, so that reconditioning fluid present in the flushed internal channels of the medical instrument 6 can be blown out from the channels.

This process takes place, for example, at the end of the reconditioning process. The internal channels of the medical instrument 6 are not only freed of the reconditioning fluid. They can also be dried by such a shot of compressed air.

The reconditioning of the medical instrument 6 can comprise multiple steps. For example, the internal channels of the medical instrument 6 can be flushed with various reconditioning fluids in multiple consecutive flushing steps. The shot of compressed air is then applied to the fluid connections 26a, 26b allocated to the medical instrument 6 between two consecutive flushing steps. This reduces the transfer of alkaline solution. In other words, only an unavoidable small quantity of reconditioning fluid is therefore transferred from one flushing step to the next.

In order to ensure that compressed air is not wasted during the application of the shot of compressed air to the fluid connections 26, the unallocated fluid connections 26c, 26d can be shut off at least during the time of the shot of compressed air, such as where all of the fluid connections 26a, 26b, 26c and 26d are supplied via a common supply line.

According to another embodiment, a further shot of compressed air can be applied to the fluid connections 26c, 26d which are not allocated to the identified type of medical instrument 6. This further shot of compressed air can last a shorter time than the shot of compressed air, with which the at least one flushed internal channel of the medical instrument 6 is blown out. The comparison of the temporal duration of the two shots of compressed air requires, for better comparability, that these be observed at the same pressure. Reconditioning fluid, which collects in the unallocated fluid connections 26c, 26d during the reconditioning process, is blown out by the further shot of compressed air. Thus, following the termination of the reconditioning process, the machine is optimally cleaned and is ready for the following and next reconditioning process, without cleaning fluid being transferred from one process to the next.

While there has been shown and described what is considered to be preferred embodiments, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE NUMERALS

2 Medical system
4 Reconditioning apparatus
6 Medical instrument
8 Door
10 Reconditioning chamber
12 Operating unit
14 Control unit
16 Compressed air unit
18 Database
20 Input unit
22 Compressed air connection
24 Identifying feature
25 Reconditioning basket
26, 26a, 26b, 26c and 26d Fluid connections
28a, 28b Connection hoses

What is claimed is:

1. A method for operating a reconditioning apparatus for cleaning and disinfecting at least one medical instrument, the at least one medical instrument having at least one internal channel, the method comprising:
   receiving the at least one medical instrument in a reconditioning chamber of the reconditioning apparatus during reconditioning;
   connecting the at least one internal channel to a fluid connection of a plurality of fluid connections provided in the reconditioning chamber;
   flushing the at least one internal channel during the reconditioning with a reconditioning fluid;
   detecting an identifying feature of the at least one medical instrument indicating information relating to a type of the at least one medical instrument;
   comparing the detected type of the at least one medical instrument with data sets stored in a database and, of a plurality of fluid connections, provide an allocation of a fluid connection connected to the at least one internal channel on a basis of the identified type;
   determining that reconditioning fluid present in the at least one internal channel should be blown out of the at least one internal channel; and
   subsequent to the flushing, actuating a compressed air source to apply compressed air to the allocated fluid connection such that the reconditioning fluid present in the at least one internal channel is blown out of the channel.

2. The method according to claim 1, wherein:
   the flushing comprises multiple flushes; and
   the actuating comprises actuating the compressed air source to apply compressed air to the allocated fluid connection between two consecutive flushes of the multiple flushes.

3. The method according to claim 1, further comprising turning off fluid connections of the plurality of fluid connections which are not allocated to the detected type of medical instrument at least for a duration of the application of compressed air to the allocated fluid connection.

4. The method according to claim 1, further comprising actuating the compressed air source to apply compressed air to fluid connections of the plurality of fluid connections which are not allocated to the detected type of medical instrument.

5. The method according to claim 4, wherein the compressed air applied to fluid connections of the plurality of fluid connections which are not allocated to the detected type of medical instrument lasts for a shorter time than a time that the compressed air is applied to the allocated fluid connection.

6. The method according to claim 1, wherein the identifying feature is a machine-readable identifying feature and the detecting comprises reading the identifying feature.

\* \* \* \* \*